United States Patent [19]

Diehl et al.

[11] Patent Number: 5,372,870
[45] Date of Patent: Dec. 13, 1994

[54] ADHESIVE COMPOSITIONS CONTAINING RADIAL BLOCK COPOLYMERS WITH BUTADIENE ENDBLOCK AND ARTICLES PRODUCED THEREFROM

[75] Inventors: Charles F. Diehl; Gary R. Marchand; Michael O. Myers; Jean M. Tancrede, all of Baton Rouge, La.

[73] Assignees: The Dow Chemical Company, Midland, Mich.; Exxon Chemical Patents, Inc., Linden, N.J.

[21] Appl. No.: 168,952

[22] Filed: Dec. 17, 1993

Related U.S. Application Data

[60] Division of Ser. No. 705,193, May 21, 1991, Pat. No. 5,292,819, which is a continuation-in-part of Ser. No. 393,545, Aug. 11, 1989, Pat. No. 5,143,968.

[51] Int. Cl.$^5$ .............................. C08L 53/02
[52] U.S. Cl. ................... 428/198; 428/286; 428/519; 428/500; 525/98; 525/314; 604/386
[58] Field of Search .............. 525/314, 98; 428/500, 428/198, 286, 519; 604/306

[56] References Cited

U.S. PATENT DOCUMENTS

| | | | |
|---|---|---|---|
| 3,149,182 | 9/1964 | Porter | 260/879 |
| 3,231,635 | 1/1966 | Holden et al. | 260/880 |
| 3,595,942 | 7/1971 | Wald et al. | 260/880 |
| 3,614,836 | 10/1971 | Snyder et al. | 36/2.5 |
| 3,700,633 | 10/1972 | Wald et al. | 260/880 B |
| 3,736,281 | 5/1973 | Russell | 260/27 R |

(List continued on next page.)

FOREIGN PATENT DOCUMENTS

| | | |
|---|---|---|
| 0306232A2 | 3/1989 | European Pat. Off. . |
| 0362850A1 | 4/1990 | European Pat. Off. . |
| 1594267 | 3/1967 | Germany . |
| 56090-849 | 12/1979 | Japan . |
| 58089-672 | 5/1983 | Japan . |
| 1447419 | 4/1974 | United Kingdom . |
| 1592358 | 12/1976 | United Kingdom . |
| 1527226 | 10/1978 | United Kingdom . |
| 956532 | 9/1982 | U.S.S.R. . |

OTHER PUBLICATIONS

Chin, "New High Styrene Content Isoprene Based Styrenic Block Copolymer," 1991 Hot Melt Symposium, pp. 43–61, 1991.

Toig et al., "Selecting Styrenic Block Copolymers for a Variety of Adhesive Applications", *Elastomerics*, Oct. 1990, pp. 44–48.

*Primary Examiner*—James J. Seidleck
*Assistant Examiner*—W. Robinson H. Clark
*Attorney, Agent, or Firm*—Pravel, Hewitt, Kimball & Krieger

[57] ABSTRACT

Radial block copolymers characterized by the formulas: (1) $(pS-pI)_nX$ and (2) $(pS-pI-pB)_nX$ where pS is polystyrene, pI is polyisoprene, pB is butadiene, X is a residue of a multifunctional coupling agent used in the production of the radial block copolymer, and n is a number greater than 2 representative of the number of branches appended to X; hot-melt adhesive compositions constituted of said radial block copolymers, and articles of manufacture produced therefrom. These copolymers possess blocks of high average molecular weight polystyrene (10,000 to 25,000) and an overall average molecular weight (90,000 to 380,000) such that when blended in requisite proportions with a compatible tackifier resin, preferably also a secondary tackifying resin or plasticizing oil, and stabilizer, superior hot-melt adhesive compositions can be formed. The hot-melt adhesive compositions possess, inter alia, superior heat resistance, superior static time to failure with low viscosity, good peel adhesion, good tack, and high ability to bond to a polyethylene or polypropylene substrate at temperatures below that which may damage the substrate.

26 Claims, No Drawings

U.S. PATENT DOCUMENTS

| | | | |
|---|---|---|---|
| 3,784,587 | 1/1974 | Chambers | 260/876 B |
| 3,949,020 | 4/1976 | Prudence | 260/879 |
| 4,096,203 | 6/1978 | St. Clair | 260/876 B |
| 4,120,915 | 10/1978 | Fodor et al. | 525/271 |
| 4,163,077 | 7/1979 | Antonsen et al. | 428/355 |
| 4,163,764 | 8/1979 | Nash | 525/2 |
| 4,172,860 | 10/1979 | Feeney et al. | 525/97 |
| 4,177,037 | 9/1978 | Himes | 260/880 B |
| 4,205,679 | 6/1980 | Repke et al. | 128/287 |
| 4,212,910 | 7/1980 | Taylor et al. | 428/35 |
| 4,294,936 | 10/1981 | Korpman | 525/93 |
| 4,419,494 | 12/1983 | Puletti et al. | 525/95 |
| 4,444,953 | 4/1984 | St. Clair | 525/98 |
| 4,485,210 | 11/1984 | Neiditch et al. | 525/271 |
| 4,540,415 | 9/1985 | Korpman | 604/390 |
| 4,785,043 | 11/1988 | Kawai et al. | 524/272 |
| 4,942,195 | 7/1990 | Flanagan et al. | 524/294 |
| 4,944,993 | 7/1990 | Raykovitz et al. | 428/290 |
| 4,944,994 | 7/1990 | Flanagan | 428/290 |
| 5,019,071 | 5/1991 | Bany et al. | 604/389 |
| 5,028,646 | 7/1991 | Miller et al. | 524/77 |
| 5,057,571 | 10/1991 | Malcolm et al. | 524/505 |
| 5,118,762 | 6/1992 | Chin | 525/314 |
| 5,149,741 | 9/1992 | Alper | 525/95 |

ADHESIVE COMPOSITIONS CONTAINING RADIAL BLOCK COPOLYMERS WITH BUTADIENE ENDBLOCK AND ARTICLES PRODUCED THEREFROM

RELATED APPLICATION

This is a division of application Ser. No. 07/705,193 filed May 21, 1991, now U.S. Pat. No. 5,292,819 which is a continuation-in-part of application Ser. No. 393,545 filed Aug. 11, 1989 now U.S. Pat. No. 5,143,968 by Charles F. Diehl, Michael O. Myers and Jean M. Tancrede, titled "Polystyrene-Polyisoprene-Polystrene Block Copolymers, Hot Melt Adhesive Compositions, And Articles Produced Therefrom."

FIELD OF THE INVENTION

This invention relates to radial block copolymers, hot-melt adhesive compositions, and articles formed or constructed therefrom. In particular, it relates to radial block copolymers constituted of resinous polystyrene block segments and resinous polydiene block segments, specifically a polyisoprene block or a predominantly polyisoprene block containing polybutadiene, and to improved hot-melt adhesive compositions formed from said block copolymers, especially adhesives of a type useful in the assembly of disposable articles, particularly disposable articles wherein the hot-melt adhesive composition is employed in the construction to bond a polyethylene or polypropylene substrate to a tissue, nonwoven fabric or absorbent fluff.

BACKGROUND

It is known to prepare hot-melt adhesive compositions from polystyrene-polyisoprene-polystyrene and polystyrene-polybutadiene-polystyrene block copolymers. Linear polystyrene-polyisoprene-polystyrene block copolymers, hot melt adhesive compositions based on these block copolymers, articles produced from these adhesives, are disclosed in U.S. patent application Ser. No. 393,545, supra. The linear polystrene-polyisoprene-polystyrene block copolymer, or linear, pS-pI-pS block copolymer, disclosed by this application is characterized by any of the formulas: (1) pI-(pS-pI)$_n$, where n is 2, or greater than 2; (2) pS-(pI-pS)$_n$, where n is 1, or greater than 1; or (3) (pS-pI)$_n$, where n is 2, or greater than 2; wherein, in any of formulas (1), (2) or (3), pS is a polystyrene block having an average molecular weight ranging from about 12,000 to about 20,000, preferably from about 14,000 to about 19,000, pI is a polyisoprene block having an average molecular weight ranging from about 30,000 to about 70,000, preferably from about 35,000 to about 60,000, the overall molecular weight of the block copolymer ranges from about 60,000 to about 110,000, preferably from about 70,000 to about 95,000, and the polystyrene block pS components are present in an amount of at least about 27 parts to about 50 parts, preferably from about 35 parts to about 45 parts, per 100 parts by weight of the block copolymer. The pS-pI-pS block copolymer, in all embodiments is characterized by the presence of a pI block, or polyisoprene block, located between two pS blocks, or polystyrene blocks which may or may not be terminal endblocks. The pS-pI-pS block copolymer can thus be either a triblock or multi-block copolymer, through the triblock copolymer is preferred.

The hot melt adhesive composition is constituted of the pS-pI-pS block copolymer, a compatible primary tackifier resin, preferably also a secondary tackifier or plasticizing resin or plasticizing oil, and stabilizer. These block copolymers, when blended in the requisite proportions with these components, produce adhesives with high shear holding power and shear adhesion failure temperature, and a low overall molecular weight sufficient to provide low viscosity. These adhesives have, inter alia, been found admirably suitable for the construction of disposable articles wherein the adhesive is applied as a continuous or discontinuous phase between members, e.g., via brushing, spraying or air-extrusion, between members to be bound together, particularly disposable articles of multi-line construction wherein the adhesive is supplied as fine parallel longitudinal strips, or as a multi-dot pattern of adhesive droplets, to bond together a moisture impervious outer polyethylene or polypropylene sheet and an inner moisture adsorbent sheet, or tissue, as used in diaper constructions. They have also been found suitable for use in the construction of sanitary napkins, bed pads, and with or without the addition of other materials, are useful for packaging and carton sealing, magazine and book lining, or book binding, or as elastic glues generally.

Adhesives formed from this type of pS-pI-pS block copolymer has been found admirably suitable, e.g., in the production of "multi-line" (or multi-dot) constructions. Hot-melt adhesives applied in the form of fine parallel longitudinal strips (or as patterns of dots) have been found to possess sufficient adhesive and cohesive strength to provide high bond strength values so that when subjected to stress the constructions cannot be easily separated. Moreover, the adhesives can withstand high mixing and application temperatures without thermal degradation and loss of adhesive properties, and have good heat and oxidation resistance on aging. The adhesives also perform well at moderate temperatures, which is required since the disposable articles are worn at body temperature; and they also perform well at higher temperatures, which is also required since the constructed articles must also be exposed to elevated temperatures during warehousing and shipping. Furthermore, these hot-melt adhesives have low adhesive viscosity such that they can be applied at low temperature in order to avoid distortion of the polyethylene or polypropylene substrates to which the adhesive is applied. Nonetheless, there remains a need for hot-melt adhesives useful in magazine and book binding, elastic gluing operations generally, hot-melt adhesive compositions useful in the assembly of multi-line constructions, and disposable articles of multi-line construction formed from improved hot-melt adhesive compositions.

OBJECTS

It is, accordingly, a primary objective of this invention to fulfill these and other needs.

A particular object of this invention is to provide novel radial block copolymers constituted of a polystyrene block segment and a polydiene block segment, viz. a polyisoprene block or a polyisoprene block containing some polybutadiene, and improved hot-melt adhesive compositions particularly useful in the assembly of disposable articles of manufacture, particularly disposable articles of multi-line construction, formed from such radial block copolymers.

A further, and more particular object is to provide hot-melt adhesive compositions which have superior heat resistance, superior static time to failure with low viscosity, good peel adhesion, and good tack and high ability to bond to a polyethylene or polypropylene substrate at temperature below that which would be injurious to the substrate.

A further, and yet more specific object is to provide disposable articles as previously described, particularly disposable articles of multi-line or multi-dot construction, wherein a polyethylene or polypropylene substrate is bonded to a tissue, or non-woven polyethylene or polypropylene substrate, or both, via the use of said improved hot-melt adhesive compositions.

THE INVENTION

These objects and others are achieved pursuant to the practice of this invention, embodying a novel radial block copolymer constituted of resinous polystyrene block segments and resinous polydiene block segments, suitably a polyisoprene block or a predominantly polyisoprene block containing a relatively small amount of polybutadiene, and a novel hot-melt adhesive composition comprising said novel copolymer, compatible primary tackifier resin, preferably also a secondary tackifier resin or plasticizing oil, and stabilizer. The hot-melt adhesive composition is, in particular, comprised of said radial block copolymers the polystyrene blocks of which are sufficiently high average molecular weight to provide, inter alia, when blended in the requisite proportions with a compatible tackifier resin, preferably also a secondary tackifier resin or plasticizing oil, and stabilizer, high shear holding power and shear adhesion failure temperature, and a low overall molecular weight sufficient to provide low viscosity.

The novel radial polystyrene-polyisoprene or polystyrene-polyisoprene/polybutadiene block copolymer is characterized by the formulas:

(1) $(pS-pI)_nX$ (2) $(pS-pI-pB)_nX$ where pS is polystyrene, pI is polyisoprene, pB is polybutadiene, X is a residue of a multifunctional coupling agent used in the production of the radial block copolymer, and n is a number greater than 2, and representative of the number of branches appended to X. The number n, for $(pS-pI)_nX$ block copolymers, will on the average range from above 2 to about 6, preferably above about 3 to about 5; and for $(pS-pI-pB)_nX$ block copolymers, on the average will range from above about 3 to about 7, preferably above about 3.5 to about 4. In either formula (1) or (2), pS is a polystyrene block having an average number molecular weight ranging from about 10,000 to about 25,000, preferably from about 14,000 to about 20,000, and pI is a polyisoprene block having an average number molecular weight ranging from about 20,000 to about 70,000, preferably from about 20,000 to about 40,000. In formula (2), pI-pB is a polyisoprene/polybutadiene block, or polyisoprene block an end of which contains butadiene, or polybutadiene, and the pI-pB component is one having a total average number molecular weight ranging from about 20,000 to about 70,000, preferably from about 20,000 to about 40,000. The overall number average molecular weight of the radical block copolymer in accordance with either formula (1) or formula (2) ranges from about 90,000 to about 380,000, preferably from about 100,000 to about 240,000, more preferably from about 120,000 to about 240,000, and the polystyrene block pS components are present in an amount of at least about 25 parts to about 50 parts, preferably from about 27 parts to about 45 parts, per 100 parts by weight of the radial block copolymer.

The radial block copolymers of this invention are thus constituted of resinous polystyrene block segments and resinous polydiene block segments, suitably, in accordance with formula (1), of polyisoprene, pI; or, in accordance with formula (2), of polyisoprene and polybutadiene, pI-pB. Thus, styrene is employed to make the resinous pS block segments of both the $(pS-pI)_nX$ and $(pS-pI-pB)_nX$ block copolymers. In accordance with formula (1), isoprene is employed to make the resinous pI block segments, the (pS-pI) polymer chains being formed by sequential polymerization of isoprene with the pS. The (pS-pI) polymer chains, suitably as pS-pI-Li living polymer chains, are coupled with coupling agents possessing at least three, and preferably four sites reactive toward carbon-lithium bonds, e.g., $SiCl_4$, to form the radical or multiblock $(pS-pI)_nX$ copolymer. In forming the radial or multiblock copolymer described by formula (2), i.e., $(pS-pI-pB)_nX$, pS-pI-pB-Li polymer chains are formed by the sequential polymerization of living pS-pI-Li polymer chains with butadiene. The radial or multi-block $(pS-pI-pB)_nX$ copolymers are correspondingly made by coupling the pS-pI-pB-Li living polymer chains with the multi- or tetra functional coupling agent, e.g., $SiCl_4$. Thus, the styrene is polymerized to form pS, the isoprene is then introduced to form pS-pI, the butadiene is then introduced to form pS-pI-pB, and the pS-pI-pB chains are then coupled with the tetrafunctional coupling agent to form the $(pS-pI-pB)_nX$ radical or multiblock polymer. In the pI-pB segment of the $(pS-pI-pB)_nX$ polymer, the polyisoprene is present in amount sufficient to impart predominantly polyisoprene characteristics, not butadiene or polybutadiene characteristics, to the polymer. Thus, in the pI-pB segments of the polymer, the weight amount of polyisoprene will exceed 50 percent of the total weight of diene in the polymer, i.e., pI/(pI+pB)>50 wt.%. Conversely, the weight amount of butadiene or polybutadiene will be less than 50 percent of the total weight of diene in the polymer, i.e., pB/(pI+pB)<50 wt.%. Preferably the polybutadiene portion of the diene segment is less than 10 percent, most preferably less than 5 percent, based on the total weight of the (pI+pB), or diene component of the polymer.

The small amount of butadiene at the end of the diene midblock is useful in that it enhances the coupling reaction in formation of the polymer, and results in a radial polymer with a higher number of branches. A further description of the process at this point will facilitate an understanding of this feature of the invention. The radial polymers of this invention are thus synthesized by first contacting styrene polymer with an initiator, suitably e.g., a sec-butyllithium initiator, in the presence of an inert diluent, e.g., cyclohexane. A living polymer is then formed, as represented e.g., by the simplified structure pS-Li. The living polystyrene polymer pS-Li is next contacted with an isoprene monomer; the resulting product being represented by the simplified structure pS-pI-Li. The living polymer is then "coupled" by reacting the pS-pI-Li with a multi-functional coupling agent, or agent which has three or more sites, e.g., $SiCl_4$, to produce a polymer with a radial or branched structure which may be represented as $(pS-pI)_nX$, where X is a residual of the multi-functional coupling agent, and n is a number greater than 2. Alternately, the living polymer pS-pI-Li can be contacted with a small amount of butadiene monomer to produce a living polymer with the structure pS-pI-pB-Li, where pB represents butadiene or polybutadiene. Coupling of the pS-pI-pB-Li with the coupling agent produces a branched block copolymer with the structure $(pS-pI-pB)_nX$. The radial polymer that is produced, using $SiCl_4$ as a coupling agent, will on the average produce $(pS-pI-pB)_nX$ polymers where n approximates 4, whereas, in contrast, in producing $(pS-pI)_nX$ polymers in an otherwise similar manner it will be found that n will more closely approximate 3. The butadiene need be added only in amount necessary to assure that the ends of all of the pI segments of the polymer chains are provided with at least one molecule of butadiene, though as suggested the butadiene can be added in larger amounts. The radial block copolymers of this invention, in either event, have been found to produce unexpectedly good hot melt adhesives when combined with suitable tackifier resins, plasticizer oils, and antioxidants.

Useful coupling agents are those possessing three or more, preferably four, sites reactive toward carbon-lithium bonds. Suitable coupling agents are those compositions of the formula $X(L)_n$ where X represents the coupling moiety residue, and L is a suitable leaving group. Exemplary of coupling agents of this type are silica halides, e.g., $SiCl_4$, or a silane compound where one or more of the halides is substituted by a hydrocarbyl group, e.g., methyl trichlorosilane; epoxy compounds, e.g., epoxidized linseed oil, epoxidized soybean oil; acrylate multi esters, e.g., pentaerythritol tetraacrylate; epoxy silanes; divinyl compounds, e.g., divinyl benzene, and the like.

The hot-melt adhesive composition is, in particular, comprised of from about 15 percent to about 35 percent, preferably from about 20 percent to about 30 percent, based on the weight of the hot-melt adhesive composition, of said radial block copolymer wherein the pI component or pI-pB component, respectively, is one having an average molecular weight ranging from about 20,000 to about 70,000, preferably from about 20,000 to about 40,000, the pS component is polystyrene having an average molecular weight ranging from about 10,000 to about 25,000, preferably from about 14,000 to about 20,000, the overall molecular weight of the block copolymer ranges from about 90,000 to about 380,000, preferably from about 100,000 to about 240,000, and wherein the pS component is present in an amount of at least about 25 parts up to about 50 parts, preferably from about 27 parts to about 45 parts, per 100 parts by weight of the radial block copolymer; from about 45 percent to about 70 percent, preferably from about 50 percent to about 60 percent, based on the weight of the hot-melt adhesive composition, of a compatible primary tackifying resin; from 0 percent to about 30 percent, preferably from about 5 percent to about 20 percent, of a plasticizing oil, or secondary tackifying resin, or both, based on the weight of the hot-melt adhesive composition; and from about 0.1 percent to about 2 percent, preferably from about 0.5 percent to about 1.5 percent of a stabilizer, based on the weight of the hot-melt adhesive composition.

These hot-melt adhesive compositions, constituted of a $(pS-pI)_nX$ or $(pS-pI-pB) X$ radial block copolymer of intermediate to relatively high styrene content and overall low molecular weight to which the primary tackifying resin, the secondary tackifying resin or plasticizing oil, and stabilizer have been added, have been found to possess properties which are admirably suitable for the construction of disposable articles wherein the adhesive is applied as a continuous or discontinuous phase, or substrate, between members, e.g., via brushing, spraying or air-extrusion, between members to be bound together, articles, particularly disposable articles of multi-line construction wherein the adhesive is applied as fine parallel longitudinal strips, swirled, or as a multi-dot pattern of adhesive droplets, to bond together a moisture impervious outer polyethlene or polypropylene sheet and an inner moisture absorbent sheet, or tissue, as used in diaper constructions. These adhesive compositions have also been found suitable for use in the contruction of sanitary napkins, bed pads, and, with or without the addition of other materials, are also useful for packaging and carton sealing, magazine and book lining, or book binding, or as elastic glues generally. These hot-melt adhesive compositions can be melted, and maintained under a blanketing nitrogen atmosphere, at relatively low to high temperatures without thermal degradation. The compositions can be applied in fluid form to polyethylene and polypropylene substrates as continuous or discontinuous films, suitably as fine lines or as patterns of multi-dots, without any risk of damage to the polyethylene or polypropylene substrate. These hot-melt adhesive compositions have also been found to serve a construction function in binding together an outer sheet, or wrapper overlapped with an absorbent pad as required in the construction of sanitary napkins. The hot-melt adhesive composition applied as a fluid permeates the overlapped area to bind and seal the absorbent pad inside the outer sheet which serves as a wrapper.

The primary tackifying resins useful in the practice of this invention include hydrocarbon resins, synthetic polyterpenes, rosin esters and natural terpenes which are semi-solid or solid at ambient temperatures, and soften or become liquid at temperatures ranging generally from about 70° C. to about 135° C., preferably from about 85° C. to about 120° C. Exemplary of the primary tackifying resins are compatible resins such as (1) natural and modified rosins such, for example, as gum rosin, wood rosin, tall oil rosin, distilled rosin, hydrogenated rosin, dimerized rosin, and polymerized rosin; (2) glycerol and pentaerythritol esters of natural and modified rosins, such, for example, as the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natured terpenes, e.g., styrene/terpene and alpha methyl styrene/terpene; (4) polyterpene resins having a softening point, as determined by ASTM method E28-58T, of from about 80° to 150° C.; the latter polyterpene resins generally resulting from the polymerization of terpene hydrocarbons, such as the bicylic monoterpene known as pinene, in the presence of Friedel-Crafts catalysts at moderately low temperatures; also included are the hydrogenated polyterpene resins; (5) phenolic modified terpene resins and hydrogenated derivatives thereof such, for example, as the resin product resulting from the condensation, in an acidic medium, of a bicyclic terpene and a phenol; (6) aliphatic petroleum hydrocarbon resins having a Ball and Ring softening point of from about 70° to 135° C.; the latter resins resulting from the polymerization of monomers consisting primarily of olefins and diolefins; also included are the hydrogenated aliphatic petroleum hydrocarbon resins; (7) aromatic petroleum hydrocarbon resins, and mixed aromatic and aliphatic paraffin hydrocarbon resins, and the hydrogenated derivatives thereof; (8) aromatic modified alicyclic petroleum hydrocarbon resins and the hydrogenated derivities thereof; and (9) alicyclic petroleum hydrocarbon resins and the hydrogenated derivatives thereof. The preferred primary tackifying resins for use in the practice of this invention are represented by sub-paragraphs (1), (3) and (7), supra. Suitable secondary tackifying resins are those named species wherein the resin is a liquid at ambient temperature.

Various plasticizing oils are useful in the practice of this invention. The plasticizing oil can be used in place of or in combination with the secondary tackifier to reduce viscosity and improve tack properties. Plasticizing oils which have been found useful include olefin oligomers and low molecular weight polymers as well as vegetable and animal oil and their derivatives. The petroleum derived oils which may be employed are relatively high boiling materials containing only a minor proportion of aromatic hydrocarbons (preferably less than 30% and, more particularly, less than 15% by weight of the oil). Alternately, the oil may be totally non-aromatic. The oligomers may be polypropylenes, polybutenes, hydrogenated polyisoprene, hydrogenated polybutadiene, polypiperylene and copolymers of piperylene and isoprene, or the like having average molecular weights between about 350 and about 10,000. Vegetable and animal oils include glyceryl esters of the usual fatty acids and polymerization products thereof.

The stabilizer, or antioxidant, used in accordance with the practice of this invention includes high molecular weight hindered phenols and multifunctional phenols such as sulfur and phosphorous-containing phenols. Hindered phenols are well known to those skilled in the art and may be characterized as phenolic compounds which also contain sterically bulky radicals in close proximity to the phenolic hydroxyl group thereof. In particular, tertiary butyl groups generally are substituted onto the benzene ring in at least one of the ortho positions relative to the phenolic hydroxy group. The presence of these sterically bulky substituted radicals in the vicinity of the hydroxyl group serves to retard its stretching frequency and, correspondingly, its reactivity; this steric hindrance thus providing the phenolic compound with its stabilizing properties. Representative hindered phenols include: 1,3,5-trimethyl 2,4,6-tris (3,5-di-tert-butyl-4-hydroxybenzyl) benzene; pentaerythrityl tetrakis-3 (3,5-di-tertbutyl-4-hydroxyphenyl) propionate; n-octadecyl-3,3,5-di-tert-butyl-4-hydroxyphenyl)propionate; 4,4′-methylenbis (2,6-tert-butylphenol); 4,4′-thiobis (6-tert-butyl-o-cresol); 2,6-di-tertbutylphenol; 6-(4-hydroxyphenoxy)-2,4-bis(n-octylthio)-1,3,5 21 triazine; di-n-octadecyl 3,5-di-tert-butyl-4-hydroxy-benzylphosphonate; 2-(n-octylthio) ethyl 3,5-di-tert-butyl-4-hydroxy-benzoate; and sorbitol [hex 3-(3,5-di-tert-butyl-4-hydroxyphenyl)propionate.]

The hot-melt adhesive composition is prepared for use by blending the radial block copolymer with the primary tackifying resin, the secondary tackifying resin or plasticizing oil, and stabilizer, in any order or sequence, or these materials can be added together simultaneously to form the adhesive composition. In commercial practice it would be expected that the primary tackifying resin and copolymer, with or without the simultaneous addition of the secondary tackifying resin or plasticizing oil, and stabilizer, would be blended together at sufficiently elevated temperature to form a fluid melt. For example, the copolymer can be blended with the solid compatible primary tackifying resin at temperatures ranging from about 130° C. to about 200° C., preferably at from about 150° C. to about 180° C., to form a fluid melt. The secondary liquid tackifying resin, or plasticizing oil, and stabilizer, can then be added to the melt. Alternatively, the fluid melt can be prepared with all components of the adhesive composition present ab initio.

The following non-limiting examples, and comparative demonstrations, bring out the more salient features of the invention. All parts are given in terms of weight units except as may otherwise be indicated.

EXAMPLES

In conducting the following tests the composition and properties of the neat radial, and linear block copolymers which were prepared for making the adhesive compositions were determined by techniques "a," "b" and "c". In evaluating the performance characteristics of the adhesive compositions produced from the radial, and linear block copolymers test procedures "d" through "f" were employed, to wit:

a. Styrene content—of the experimental radial, and linear block copolymers was determined from the proton nmr spectra. Samples were dissolved in a mixture of deuterated tetrachlroethane/tetrachloroethylene, and analyzed on a Bruker 90 MHz spectrometer. Styrene content was calculated from the spectra by the method of V. D. Mochel, *Rubber Chem. and Tech.*, 34 40, 1200 (1967).

b. Molecular Weight—of the experimental radial, and linear block copolymers was determined by GPC, using the method described by J. R. Runyon, et al, *J. Polym. Sci.* 13, 2359 (1969).

c. Melt Flow Rate (MFR)—of the experimental radial, and linear block copolymers was determined according to ASTM method D-1238-82, using condition "G" (200° C., 5 Kg weight).

d. Adhesive Melt Viscosity (ASTM D-3236)—Melt viscosities were measured at a temperature of 130° C., using a Brookfield Thermosel viscometer. Low adhesive viscosities are a necessity for processing in multi-line, spray, and fiberization equipment. In addition, the viscosity must be low at relatively low processing temperatures in order to avoid distortion of the polyolefin backing when hot adhesive is applied.

e. Shear Adhesion Failure Temperature (SAFT)—is a measure of the ability of the bond to withstand an elevated temperature rising at 10° F./15 min., under a constant force which pulls the bond in the shear mode. Bonds 1 inch by 1 inch were formed of adhesive, on a Mylar (polyester) backing, to a stainless steel panel, using a 4.5 lb. rubber roller. The panel was suspended vertically in an oven at 32° C., and allowed to come to equilibrium. A 1 kg weight was suspended from the free end of the adhesive tape, and the temperature was raised at 10° F./15 min. The temperature at which the tape and weight fell from the panel was recorded. SAFT was reported as the average of three such determinations. Adhesives possessing high failure temperatures are essential for the assembly of disposable articles, which are often subjected to very high temperatures during storage and shipping. In addition, these articles are used (worn) at body temperature.

f. Shear Holding Power (Static Time to Failure Bond Test)—The cohesive strength of the adhesives was determined according to the general procedures outlined in PSTC-7 and ASTM D-3654. A 1 inch by 0.5 inch bond was applied to a stainless steel panel with a 4.5 lb rubber roller. The plate was suspended vertically and allowed to equilibrate at 35° C. A 1 Kg weight was suspended from the free end of the tape. The time at which the tape and weight fell from the panel was recorded. The shear hold (in min) was reported as the average of four such determinations. Long failure times are desirable, since they indicate strong bonds, which are essential in certain areas of the disposable constructions, which are subjected to considerable stress during use.

Examples 1–4, which immediately follow, describe the synthesis, and certain characteristics of the (pS-pI-pB)$_n$X radial polymers of this invention. Examples 5–7, on the other hand, describe the synthesis and certain characteristics of the (pS-pI)$_n$X radial polymers of this invention. Demonstration 9 is a linear pS-pI-pS linear block copolymer of the type described in application Ser. No. 393,545, supra; the performance of which when made into an adhesive is substantially equivalent to that of the radial block copolymers of this invention. Demonstration 8 is a radial styrene-butadiene block copolymer which has a styrene content comparable to that of the copolymers of this invention, but an adhesive produced therefrom has a SAFT performance which is inferior to the radial polymers of this invention. Additionally, for comparative purposes, Demonstrations 10–12 represent polymers obtained from commercial sources, formulated into adhesive compositions, and tested. Demonstration 10 thus describes the performance characteristics of an adhesive composition formed from a radial polystyrene-polybutadiene copolymer produced by Shell Chemical Company; Demonstration 11 an adhesive composition formulated from a linear multiblock polystyrene-polybutadiene copolymer produced by Firestone Tire and Rubber Company; and Demonstration 12 an adhesive composition formed from a linear polystyrene-polyisoprene-polystyrene copolymer produced by Enichem Americas, Inc.

The preparation of the block copolymers, and certain characteristics of the block copolymers, as employed in Examples 1 through 7 and Demonstration 8 and 9 are given as follows:

Example 1 (5145–45)

To a 5-gallon, stirred reactor under a nitrogen atmosphere were added 12.6 kg of cyclohexane and 905 g of styrene. The temperature of the reactor was brought to 50° C. and 147 g of a 0.28M solution of sec-butyllithium in cyclohexane was added. Polymerization was allowed to continue for 50 minutes. The reaction mixture was cooled to 50° C. and 1148 g of isoprene was added. The isoprene was allowed to polymerize for 32 minutes during which the reaction temperature reached a maximum of 68° C. At the end of the 32 minutes, 34 g of butadiene was added and it was allowed to polymerize for an additional 30 minutes. Then 14 g of SiCl$_4$ was added slowly over the course of 11 minutes. The reaction was allowed to continue for another 15 minutes before an excess of isopropanol was added to the reaction mixture to quench any residual Li alkyl. A hindered phenol antioxidant was added to the polymer solution which was then devolatilized in a vacuum oven under nitrogen at 100° C. for 3 hours.

Size exclusion chromatography of the resultant polymer showed two peaks, a high molecular weight peak which was the radial or star shaped polymer comprising 78% of the total polymer and a lower molecular weight peak, comprising 22% of the total polymer, which was the diblock building block before coupling the chain ends using SiCl$_4$. From gel-permeation chromatography, GPC, it was estimated that each arm of the radial polymer was composed of a polystyrene block of 18,000 molecular weight and 22,800 molecular weight polydiene. The melt flow rate was 61.8. Ultimate tensile of the material was 2763 psi.

Example 2 (5146-14)

To a 5-gallon, stirred reactor under a nitrogen atmosphere were added 12.6 kg of cyclohexane and 718 g of styrene. The temperature of the reactor was brought to 50° C. and 134.6 g of a 0.317M solution of sec-butyllithium in cyclohexane was added. Polymerization was allowed to continue for 60 minutes. The reaction mixture was cooled to 50° C. and 1328 g of isoprene was added. The isoprene was allowed to polymerize for 25 minutes during which the reaction temperature reached a maximum of 77° C. At the end of the 25 minutes, 34 g of butadiene was added and it was allowed to polymerize for an additional 18 minutes. Then 13 g of SiCl$_4$ was added slowly over the course of 6 minutes. The reaction was allowed to continue for another 19 minutes before an excess of isopropanol was added to the reaction mixture to quench any residual Li alkyl. A hindered phenol antioxidant was added to the polymer solution which was then devolatilized in a vacuum oven under nitrogen at 100° C. for 3 hours.

Size exclusion chromatography of the resultant polymer showed two peaks, a high molecular weight peak which was the radial or star shaped polymer comprising 86% of the total polymer and a lower molecular weight peak, comprising 14% of the total polymer, which was the diblock building block before coupling the materials using SiCl$_4$. From the GPC it was estimated that each arm of the radial polymer was composed of a polystyrene block of 16,560 molecular weight and 30,620 molecular weight polydiene. The melt flow rate was 18.7. Ultimate tensile of the material was 4430 psi.

Example 3 (5146-13)

To a 5-gallon, stirred reactor under a nitrogen atmosphere were added 12.6 kg of cyclohexane and 970 g of styrene. The temperature of the reactor was brought to 50° C. and 139.0 g of a 0.317M solution of sec-butyllithium in cyclohexane was added. Polymerization was allowed to continue for 88 minutes. The reaction mixture was cooled to 50° C. and 1086 g of isoprene was added. The isoprene was allowed to polymerize for 39 minutes during which the reaction temperature reached a maximum of 66° C. At the end of the 39 minutes, 34 g of butadiene was added and it was allowed to polymerize for an additional 33 minutes. Then 13 g of SiCl$_4$ was added slowly over the course of 8 minutes. The reaction was allowed to continue for another 18 minutes before an excess of isopropanol was added to the reaction mixture to quench any residual Li alkyl. A hindered phenol antioxidant was added to the polymer solution which was then devolatilized in a vacuum oven under nitrogen at 100° C. for 3 hours.

Size exclusion chromatography of the resultant polymer showed two peaks, a high molecular weight peak which was the radial or star shaped polymer comprising 87% of the total polymer and a lower molecular weight peak, comprising 13% of the total polymer, which was the diblock building block before coupling the materials using $SiCl_4$. From the GPC it was estimated that each arm of the radial polymer was composed of a polystyrene block of 20,960 molecular weight and 23,440 molecular weight polydiene. The melt flow rate was 29.4. Ultimate tensile of the material was 3316 psi.

Example 4 (5146-16)

To a 5-gallon, stirred reactor under a nitrogen atmosphere were added 12.6 kg of cyclohexane and 851 g of styrene. The temperature of the reactor was brought to 50° C. and 121.8 g of 0.317M solution of sec-butyllithium in cyclohexane was added. Polymerization was allowed to continue for 54 minutes. The reaction mixture was cooled to 50° C. and 1200 g of isoprene was added. The isoprene was allowed to polymerize for 31 minutes during which the reaction temperature reached a maximum of 74° C. At the end of the 31 minutes, 34 g of butadiene was added and it was allowed to polymerize for an additional 20 minutes. Then 12 g of $SiCl_4$ was added slowly over the course of 6 minutes. The reaction was allowed to continue for another 16 minutes before an excess of isopropanol was added to the reaction mixture to quench any residual Li alkyl. A hindered phenol antioxidant was added to the polymer solution which was then devolatilized in a vacuum oven under nitrogen at 100° C. for 3 hours.

Size exclusion chromatography of the resultant polymer showed two peaks, a high molecular weight peak which was the radial or star shaped polymer comprising 87% of the total polymer and a lower molecular weight peak, comprising 13% of the total polymer, which was the diblock building block before coupling the materials using $SiCl_4$. From the GPC it was estimated that each arm of the radial polymer was composed of a polystyrene block of 20,730 molecular weight and 29,200 molecular weight polydiene. The 20 melt flow rate was 21.9. Ultimate tensile of the material was 3500 psi.

Example 5 (5280-18)

To a 5-gallon, stirred reactor under a nitrogen atmosphere were added 12.6 kg of cyclohexane and 901 g of styrene. The temperature of the reactor was brought to 50° C. and 129.2 g of a 0.317M solution of sec-butyllithium in cyclohexane was added. Polymerization was allowed to continue for 55 minutes. The reaction mixture was cooled to 50° C. and 1147.1 g of isoprene was added. The isoprene was allowed to polymerize for 31 minutes during which the reaction temperature reached a maximum of 69° C. At the end of the 31 minutes, 23.7 g of $SiCl_4$ was added slowly over the course of 6 minutes. The reaction was allowed to continue for another 30 minutes before an excess of isopropanol was added to the reaction mixture to quench any residual Li alkyl. A hindered phenol antioxidant was added to the polymer solution which was then devolatilized in a vacuum oven under nitrogen at 100° C. for 3 hours.

Size exclusion chromatography of the resultant polymer showed two peaks, a high molecular weight peak which was the radial or star shaped polymer comprising 82.2% of the total polymer and a lower molecular weight peak, comprising 17.8% of the total polymer, which was the diblock building block before coupling the materials using $SiCl_4$. From the GPC it was estimated that each arm of the radial polymer was composed of a polystyrene block of 21,021 molecular weight and 26,755 molecular weight polyisoprene. The melt flow rate was 8.1 g/10 minutes. Ultimate tensile of the material was 3620 psi.

Example 6 (5280-19)

To a 5-gallon, stirred reactor under a nitrogen atmosphere were added 12.6 kg of cyclohexane and 714.8 g of styrene. The temperature of the reactor was brought to 50° C. and 111.7 g of a 0.317M solution of sec-butyllithium in cyclohexane was added. Polymerization was allowed to continue for 53 minutes. The reaction mixture was cooled to 50° C. and 1327.4 g of isoprene was added. The isoprene was allowed to polymerize for 41 minutes during which the reaction temperature reached a maximum of 74° C. At the end of the 41 minutes, 20.5 g of $SiCl_4$ was added slowly over the course of 6 minutes. The reaction was allowed to continue for another 30 minutes before an excess of isopropanol was added to the reaction mixture to quench any residual Li alkyl. A hindered phenol antioxidant was added to the polymer solution which was then devolatilized in a vacuum oven under nitrogen at 100° C. for 3 hours.

Size exclusion chromatography of the resultant polymer showed two peaks, a high molecular weight peak which was the radial or star shaped polymer comprising 78.7% of the total polymer and a lower molecular weight peak, comprising 21.3% of the total polymer, which was the diblock building block before coupling the materials using $SiCl_4$. From the GPC it was estimated that each arm of the radial polymer was composed of a polystyrene block of 19,138 molecular weight and 35,541 molecular weight polyisoprene. The melt flow rate was 5.7 g/10 minutes. Ultimate tensile of the material was 4210 psi.

Example 7 (5280-20)

To a 5-gallon, stirred reactor under a nitrogen atmosphere were added 12.6 kg of cyclohexane and 964.2 g of styrene. The temperature of the reactor was brought to 50° C. and 118.5 g of a 0.317M solution of sec-butyllithium in cyclohexane was added. Polymerization was allowed to continue for 53 minutes. The reaction mixture was cooled to 50° C. and 1087.3 g of isoprene was added. The isoprene was allowed to polymerize for 35 minutes during which the reaction temperature reached a maximum of 69° C. At the end of the 35 minutes, 21.8 g of $SiCl_4$ was added slowly over the course of 6 minutes. The reaction was allowed to continue for another 32 minutes before an excess of isopropanol was added to the reaction mixture to quench any residual Li alkyl. A hindered phenol antioxidant was added to the polymer solution which was then devolatilized in a vacuum oven under nitrogen at 100° C. for 3 hours.

Size exclusion chromatography of the resultant polymer showed two peaks, a high molecular weight peak which was the radial or star shaped polymer comprising 84.8% of the total polymer and a lower molecular weight peak, comprising 15.2% of the total polymer, which was the diblock building block before coupling the materials using $SiCl_4$. From the GPC it was estimated that each arm of the radial polymer was composed of a polystyrene block of 24,534 molecular weight and 27,666 molecular weight polyisoprene. The melt flow rate was 8.9 g/10 minutes. Ultimate tensile of the material was 3340 psi.

Demonstration 8 (5145-49)

To a 5-gallon, stirred reactor under a nitrogen atmosphere were added 12.5 kg of cyclohexane and 911.6 g of styrene. The temperature of the reactor was brought to 50° C. and 170.8 g of a 0.317M solution of sec-butyllithium in cyclohexane was added. Polymerization was allowed to continue for 46 minutes. The reaction mixture was cooled to 50° C. and 1123 g of butadiene was added. The butadiene was allowed to polymerize for 46 minutes during which the reaction temperature reached a maximum of 69° C. At the end of the 46 minutes, 21.5 g of $SiCl_4$ was added slowly over the course of 10 minutes. The reaction was allowed to continue for another 17 minutes before an excess of isopropanol was added to the reaction mixture to quench any residual Li alkyl. A hindered phenol antioxidant was added to the polymer solution which was then devolatilized in a vacuum oven under nitrogen at 100° C. for 3 hours.

Size exclusion chromatography of the resultant polymer showed two peaks, a high molecular weight peak which was the radial or star shaped polymer comprising 76.3% of the total polymer and a lower molecular weight peak, comprising 23.7% of the total polymer, which was the diblock building block before coupling the materials using $SiCl_4$. From the GPC it was estimated that each arm of the radial polymer was composed of a polystyrene block of 15,635 molecular weight and 19,264 molecular weight polybutadiene. The melt flow rate was 28.8 g/10 minutes.

Demonstration 9 (5054-30)

To a 2.6 liter reactor were charged 1499 g of cyclohexane and 85.8 g of styrene monomer. The mixture was heated to 60° C. and 7.8 ml of a 0.70 molar solution of sec-butyllithium initiator in cyclohexane was added. After 41 minutes, the reaction temperature was reduced to 58° C. and 118.5 grams of isoprene was added. After 39 minutes the living styrene-isoprene diblock polymer was coupled to form a linear styrene-isoprene-styrene triblock polymer by adding 32 ml of 0.12M 1,2-dibromoethane in cyclohexane over a period of 11 minutes. A hindered phenol antioxidant was added to the polymer solution which was then devolatized in a vacuum oven under nitrogen at 100° C. for 3 hours.

Size exclusion chromatography of the resultant polymer showed two peaks, a high molecular weight peak which was the linear triblock polymer comprising 86.5% of the total polymer and a lower molecular weight peak, comprising 13.5% of the total polymer, which was the diblock building block before coupling the chain ends using DBE. From the GPC it was estimated that the molecular weight of the styrene blocks was 16,660, and the molecular of the polyisoprene midblock was 42,580. The melt flow rate was 50 g/10 minutes.

Adhesive compositions were prepared by combining 100 parts of the block copolymer, 220 parts of the primary tackifying resin (Zonatac 105L, available from Arizona Chemical), 80 parts of Tufflo 6056 (a plasticizer oil available from Lyondell Petroleum Company), and 3 parts of Irganox 1010 (a stabilizer available from Ciba-Geigy), to produce a homogeneous adhesive blend. The adhesive was coated on 2 mil thick Mylar (polyester) backing, to produce a 1.5 mil thick film, of adhesive.

The performance characteristics of the adhesives of the block copolymers are given in the Table, the adhesive formulations for the $(pS-pI-pB)_nX$ and $(pS-pI)_nX$ radial block copolymers, or "rubbers" of this invention, designated as Examples 1 through 7, being set out for comparison with adhesive formulations prepared from rubbers not of this invention, i.e., Demonstrations 8–12. Columns 1 and 2 of the Table identifies the specific test run and type of rubber tested. Columns 3–6 identifies the MFR, or Melt Flow Rate, the total wt. % styrene content of the rubber, the molecular weight of the polystyrene block component of a rubber, pS, and the molecular weight of the polyisoprene block component of a rubber, pI. Columns 7–9 describe the results of the tests conducted on each of the adhesive formulations, viz. the adhesive viscosity, SAFT, and the holding power. It is clear that the adhesive compositions of this invention, i.e., Examples 1–7, exhibit superior SAFT (high temperature resistance), and superior holding power (static time to failure).

TABLE

| ADHESIVE FORMULATION: | PHR |
| --- | --- |
| Block Copolymer (RUBBER) | 100 |
| Primary Tackifier (ZONATAC 105L) | 220 |
| Plasticizer Oil (TUFFLO 6056) | 80 |
| Stabilizer (IRGANOX 1010) | 3 |

| RUBBER | TYPE | MFR | WT % STYRENE | POLYSTYRENE MOL WT | POLYDIENE (pD) MOL WT | ADHES. VISC. 130° C. (CPS) | SAFT (°C.) | 35° C. HOLD (MIN) |
| --- | --- | --- | --- | --- | --- | --- | --- | --- |
| EXAMPLE 1 | (pS-pI-pB)n-X | 61.8 | 44.1 | 18006 | 22823 | 7538 | 83.6 | >4000 |
| EXAMPLE 2 | (pS-pI-pB)n-X | 18.7 | 35.1 | 16561 | 30621 | 7425 | 80.4 | >4000 |
| EXAMPLE 3 | (pS-pI-pB)n-X | 29.4 | 47.2 | 20955 | 23441 | 17425 | 88.7 | >4000 |
| EXAMPLE 4 | (pS-pI-pB)n-X | 40.3 | 41.5 | 20726 | 29216 | 13325 | 88.1 | >4000 |
| EXAMPLE 5 | (pS-pI)n-X | 8.1 | 45.3 | 21021 | 26755 | 14425 | 84.4 | >4000 |
| EXAMPLE 6 | (pS-pI)n-X | 5.7 | 35.3 | 19138 | 35541 | 18700 | 80.9 | >4000 |
| EXAMPLE 7 | (pS-pI)n-X | 8.9 | 47.1 | 24534 | 27666 | 17500 | 88.6 | >4000 |
| DEMONSTRATION 8 | (pS-pB)n-X | 28.8 | 44.8 | 15635 | 19264 | 9050 | 76.8 | >4000 |
| DEMONSTRATION 9 | pS-pI-pS | 50 | 43.9 | 16660 | 42580 | 8875 | 83.2 | >4000 |
| DEMONSTRATION 10 (KRATON D1122) | (pS-pB)n-X | 3.3 | 39.7 | 14211 | 21585 | 15350 | 72.6 | >4000 |
| DEMONSTPATION 11 (STEREON 840A) | (pS-pB)n-pS | 12.4 | 42.3 | | | 9575 | 68.3 | 453 |
| DEMONSTRATION 12 (EUROPRENE | pS-pI-pS | 12.8 | 24.2 | 13189 | 82622 | 7650 | 68.7 | 395 |

TABLE-continued

SOLT193B)

LEGEND:
pS = POLYSTYRENE BLOCK
pI = POLYISOPRENE BLOCK
pB = POLYBUTADIENE BLOCK
pD = POLYDIENE BLOCK = (pI + pB)
NOTES:
(1) KRATON is a trademark of Shell Chemical Company
(2) STEREON is a trademark of Firestone Tire and Rubber Company
(3) EUROPRENE is a trademark of Enichem Americas, Inc.

Continuing reference to the Table, Examples 1 through 7 show the performance of adhesive compositions prepared from radial block polymers whose % styrene, polystyrene molecular weight, and polydiene molecular weight are all within the preferred ranges of the radial block copolymer required for the practice of this invention. It is required that all of these parameters fall within the ranges expressed in order to obtain this superior adhesive performance. Comparative Example 8, showing the performance characteristics of an adhesive composition of a radial styrene-butadiene copolymer not of this invention, albeit the copolymer has a styrene content and melt flow rate comparable to the radial copolymers of this invention, is inadequate. Its shear adhesion failure temperature, SAFT, is very poor. Styrene-isoprene copolymers have inherently lower viscosity than styrene-butadiene copolymers of the same molecular weight, and hence the styrene-isoprene copolymers are superior in that they can be made with higher molecular weight pS blocks. As a result, the styrene-isoprene copolymers can be produced with greater SAFT. Comparative Example 9 shows the performance characteristics of an adhesive composition made from a linear pS-pI-pS copolymer as disclosed in application Ser. No. 393,545, supra. Demonstrations 10, 11 and 12 represent adhesive compositions prepared from commercially available copolymers having properties which fall outside those requirements which are necessary to obtain superior hot-melt adhesives, i.e., a radial (pS-pB)nX block copolymer as represented by Demonstrations 10 (Kraton D 1122), a (pS-pB)n pS linear multiblock copolymer as represented by Demonstration 11 (Stereon 34 840A), and a linear pS-pI-pS block copolymer as represented by Demonstration 12 (Europrene SOL T 193 B). As shown by the Table, the adhesive compositions of Example 1 through 7 clearly exhibit the best combination of low adhesive viscosity, high SAFT, and high 35° C. Hold.

A prepared adhesive composition useful for magazine or book binding can also be formed from the hot-melt adhesive composition of this invention by the further addition to the hot-melt adhesive composition of from 0 to about 5 percent, preferably from about 0.5 to about 5 percent, based on the weight of the hot-melt adhesive composition, of a hydrocarbon or petroleum derived wax. Exemplary petroleum derived waxes are, e.g., paraffin and microcrystalline waxes having melting points within a range of from about 55° C. to about 110° C., as well as low molecular weight polyethylene and Fischer-Tropsch waxes.

It is apparent that various modifications and changes can be made without departing the spirit and scope of the invention.

Having described the invention, what is claimed is:

1. An adhesive composition which comprises:
   a radial block copolymer containing a polystyrene block segment and a polyisoprene block segment having an end which comprises butadiene, wherein the block copolymer is characterized by the formula:

$(pS-pI-pB)_nX$ wherein pS is polystyrene, pI is polyisoprene, pB is polybutadiene, X is the residue of a multifunctional coupling agent used in the production of the radial block copolymer and n is a number greater than 2 and represents the number of branches appended to X;
   pS has an average number molecular weight ranging from about 10,000 to about 25,000, pI+pB has an average number molecular weight ranging from about 20,000 to about 70,000, the overall number average molecular weight of the block copolymer ranges from about 90,000 to about 380,000, and wherein the pS component is present in an amount of at least 25 parts to about 50 parts per 100 parts by weight of the radial block copolymer;
   a compatible primary tackifying resin; and
   a stabilizer.

2. The composition of claim 1 wherein the composition contains from about 15 percent to about 35 percent of the copolymer.

3. The composition of claim 1 wherein the composition contains from about 45 percent to about 70 percent of the compatible primary tackifying resin.

4. The composition of claim 1 which further contains from about 5 percent to about 20 percent of a plasticizing oil or secondary tackifying resin.

5. The composition of claim 1 wherein the adhesive composition contains from about 0.1 percent to about 2 percent of the stabilizer.

6. The composition of claim 1 wherein the average molecular weight of the pI+pB component of the radial block copolymer ranges from about 20,000 to about 40,000, the average molecular weight of the pS component ranges from about 14,000 to about 20,000 and the overall molecular weight of the copolymer ranges from about 100,000 to about 240,000.

7. The composition of claim 1 which additionally contains up to about 5 percent, based on the weight of the composition, of a hydrocarbon wax sufficient to form an adhesive composition useful for lining magazines or books, or for packaging and carton sealing.

8. The composition of claim 1 wherein n is greater than or equal to 3.

9. The composition of claim 8 wherein n on the average ranges from about 3 to about 7.

10. The composition of claim 1 wherein the pS component is present in an amount ranging from about 27 parts to about 45 parts per 100 parts by weight of the copolymer.

11. The composition of claim 6 wherein the overall number average molecular weight of the block copolymer is between about 120,000 to about 200,000.

12. The composition of claim 1 wherein X is —Si.

13. The composition of claim 1 wherein the weight amount of polybutadiene in the block pI-pB is less than 10 weight percent.

14. The composition of claim 13 wherein the weight amount of polybutadiene in the block pI-pB is less than 5 weight percent.

15. A disposable article comprising a polyethylene or polypropylene substrate bonded to a tissue, moisture absorbent fabric or absorbent fluff by use of the adhesive composition of claim 1.

16. The article of manufacture according to claim 15 wherein the moisture absorbent fabric or fluff is a nonwoven fabric.

17. The article of manufacture according to claim 15 where the adhesive composition further contains a plasticizing oil or secondary tackifying resin.

18. The article of manufacture according to claim 15 wherein the adhesive composition contains from about 15 percent to about 35 percent of the radial block copolymer.

19. The article of manufacture according to claim 15 wherein the adhesive composition contains from about 45 percent to about 70 percent of the compatible primary tackifying resin.

20. The article of manufacture according to claim 17 wherein the adhesive composition contains from about 5 percent to about 30 percent of the plasticizing oil or secondary tackifying resin.

21. The article of manufacture according to claim 15 wherein the adhesive composition contains from about 0.1 percent to about 2 percent of the stabilizer.

22. The article of manufacture according to claim 15 wherein the average molecular weight of the pI+pB component of the radial block copolymer ranges from about 20,000 to about 40,000, the average molecular weight of the pS component ranges from about 14,000 to about 20,000, the overall molecular weight of the copolymer ranges from about 100,000 to about 240,000, and wherein the pS component is present in an amount ranging from about 27 parts to about 45 parts per 100 parts by weight of the copolymer.

23. The article of manufacture according to claim 15 wherein the disposable article is selected from diapers, sanitary napkins and bed pads.

24. The article of manufacture according to claim 15 wherein the adhesive component of the disposable article is applied as a continuous or discontinuous phase.

25. The article of manufacture according to claim 15 wherein the disposable article is of multi-line construction.

26. The article of manufacture according to claim 25 wherein the adhesive component used in forming the disposable article is applied as fine parallel longitudinal strips, swirl or as a multi-dot pattern of adhesive droplets.

* * * * *